US008529914B2

(12) United States Patent
Fuisz et al.

(10) Patent No.: US 8,529,914 B2
(45) Date of Patent: Sep. 10, 2013

(54) BIOACTIVE DOSE HAVING CONTAINING A MATERIAL FOR MODULATING PH OF A BODILY FLUID TO HELP OR HINDER ABSORPTION OF A BIOACTIVE

(76) Inventors: Richard C. Fuisz, Beverly Hills, CA (US); Joseph M. Fuisz, Surfside, FL (US)

( * ) Notice: Subject to any disclaimer, the term of this patent is extended or adjusted under 35 U.S.C. 154(b) by 0 days.

(21) Appl. No.: 12/874,632

(22) Filed: Sep. 2, 2010

(65) Prior Publication Data
US 2011/0318391 A1 Dec. 29, 2011

Related U.S. Application Data

(63) Continuation-in-part of application No. 12/824,803, filed on Jun. 28, 2010, now abandoned.

(51) Int. Cl.
*A61K 9/00* (2006.01)
*A61K 36/81* (2006.01)
*A61K 31/465* (2006.01)
*A24F 23/02* (2006.01)

(52) U.S. Cl.
USPC ............ 424/400; 131/271; 131/352; 514/343

(58) Field of Classification Search
USPC ......................................... 424/400
See application file for complete search history.

(56) References Cited

U.S. PATENT DOCUMENTS

| 5,580,578 | A  | * | 12/1996 | Oshlack et al. | 424/468 |
|-----------|----|---|---------|----------------|---------|
| 6,383,471 | B1 | * | 5/2002  | Chen et al.    | 424/45  |
| 2002/0102304 | A1 |  | 8/2002  | Pinney et al.  |         |
| 2004/0037879 | A1 | * | 2/2004  | Adusumilli et al. | 424/468 |
| 2004/0109894 | A1 |  | 6/2004  | Shefer et al.  |         |
| 2004/0194793 | A1 | * | 10/2004 | Lindell et al. | 131/270 |
| 2004/0209961 | A1 |  | 10/2004 | Devane         |         |
| 2005/0031677 | A1 | * | 2/2005  | Pather et al.  | 424/448 |
| 2005/0095299 | A1 |  | 5/2005  | Wynn et al.    |         |
| 2007/0269386 | A1 | * | 11/2007 | Steen et al.   | 424/48  |
| 2008/0029110 | A1 | * | 2/2008  | Dube et al.    | 131/275 |
| 2009/0149446 | A1 |  | 6/2009  | Heldman        |         |
| 2009/0258066 | A1 | * | 10/2009 | Venkatesh et al. | 424/462 |
| 2010/0218779 | A1 | * | 9/2010  | Zhuang et al.  | 131/274 |

FOREIGN PATENT DOCUMENTS

| WO | WO 02/064109 A2 * | 8/2002 |
| WO | WO 2008/025791 A1 * | 3/2008 |
| WO | WO 2009/036340 |  3/2009 |

OTHER PUBLICATIONS

Sharma et al., Aliment Pharmacol Ther, 2000, 14: 887-892.*
"Suboxone and Subutex-sublingual tablets, last revised Sep. 2006. pdf".*
Appendix H, pKa's of Drugs and reference compounds; [online] retrieved from web.squ.edu.om on Aug. 13, 2012; 14 pages.*
Kaufman et al. (J. Med. Chem 1975, 18(7), pp. 647-655).*
MSDS for sodium tripolyphosphate 2012; 5 pages.*
Capsule [online] retrieved on Apr. 16, 2013 from: http://www.merriam-webster.com/dictionary/capsule; 5 pages.*
International Search Report and Written Opinion, PCT/US2011/041944 (Richard C. Fuisz), Dec. 30, 2011.
International Preliminary Report on Patentability, PCT/US2011/041944 (Nov. 26, 2012).

* cited by examiner

*Primary Examiner* — Ernst Arnold
(74) *Attorney, Agent, or Firm* — Antonelli, Terry, Stout & Kraus, LLP.

(57) ABSTRACT

A bioactive dose for delivering a bioactive agent to a mammal, includes a solid bioactive dosage unit containing at least one bioactive agent and a rapid release coating provided on at least one outer surface of the solid bioactive dosage unit, the rapid release coating containing a material having a property of rapidly modulating a pH of bodily fluids in which the material comes in contact in a direction towards an ideal absorptive pH or towards an ideal pH to hinder absorption of the at least one bioactive agent given the pKa that least at one bioactive agent.

16 Claims, No Drawings

BIOACTIVE DOSE HAVING CONTAINING A MATERIAL FOR MODULATING PH OF A BODILY FLUID TO HELP OR HINDER ABSORPTION OF A BIOACTIVE

CROSS-REFERENCE TO RELATED APPLICATION

This application is a continuation-in-part application of U.S. application Ser. No. 12/824,803, filed Jun. 28, 2010 now abandoned.

BACKGROUND OF THE INVENTION

It is well known in the art that from a pharmacological standpoint pH has a significant effect on drug absorption. It is generally accepted that non-parenterally, non-ionized drug is best absorbed compared to its ionized version. A common term in pharmaceuticals is the pKa, which is the pH at which 50% is ionized and 50% is non-ionized, and therefore a critical pH with respect to absorption relative to whether the drug is a weak acid or a weak base, keeping the Henderson Hasselbach equation in mind (see http://manuelsweb.com/pka.htm). The sum of pKa and pKb equals 14 at 25° C. in an aqueous solution. As set forth in http://www.sciencechatforum.com/viewtopic.php?=38&t=11464, the contents of which are incorporated herein by reference, most drugs are weak organic acids or bases, existing in un-ionized and ionized forms in an aqueous environment. The un-ionized form is usually lipid soluble and diffuses readily across cell membranes. The ionized form cannot penetrate the cell membrane easily because of its low lipid solubility and high electrical resistance, resulting from its charge and the charged groups on the cell membrane surface. Thus, drug penetration may be attributed mostly to the un-ionized form. Now this pKa applies at all areas of drug absorption, whether mucosally, in the mouth, or in the later regions of the GI tract. It is also applicable to vaginal, nasal, rectal and ophthalmic, aural, respiratory and other sites of drug delivery which are non-parenteral. This is subject to absorption principles relative to lipid solubility and water solubility. Generally the pH is controlled by the internal dosage form's dynamic buffer systems. By internal, we mean that one or more buffering agents are included in the original composition (e.g. tablet granulation, sheet extrusion mass, film casting liquid, capsule and liquigel contents etc.) and are uniformly present throughout the dosage form. As a result, such buffering agents are released at the same rate as the active ingredient and other excipients as the dosage form disintegrates which of coarse it must do to be absorbed.

DISCLOSURE OF THE INVENTION

The present invention relates to a bioactive dose for delivering a bioactive agent to a mammal includes a solid bioactive dosage unit containing at least one bioactive agent and a rapid release coating provided on at least one outer surface (or functioning as a non-enteric outer layer) of the solid bioactive dosage unit. The rapid release coating contains a material having a property of rapidly modulating a pH of bodily fluids in which the material comes in contact in a direction towards a pH which is most suitable for absorption considering the pKa of the at least one bioactive agent or alternatively towards a pH which is most suitable for retardation of absorption. This pH modifier precedes any internal dynamic buffer system which is typically used.

In another embodiment, e.g., to aid oral quick dissolve forms, such as quick dissolve films which are intended to dissolve in the mouth but for which it may not be desirable to absorb the bioactive in the mouth, the pH coating can condition to hinder the absorption. In this embodiment, the rapid release coating contains a material having a property of rapidly modulating a pH of bodily fluids in which the material comes in contact in a direction toward the least effective absorptive pH in keeping with the Henderson Hasselbach equation. On the other hand the pH coating can condition to increase the absorption in the mouth. In this embodiment, the rapid release coating contains a material having a property of rapidly modulating a pH of bodily fluids in which the material comes in contact in a direction toward the most effective absorptive pH in keeping with the Henderson Hasselbach equation.

Furthermore, this invention relates to the use of a modified liquid that contains an immediately acting pH modifier for use either contemporaneously with, prior to, or following the administration of a solid dosage form, with a view towards facilitating (or retarding) absorption. This liquid can be a base or water or a liquid which aids in swallowing (Fuisz U.S. Pat. No. 6,337,083, the contents of which are incorporated herein by reference) or in some cases the use of a flavorant liquid such as Flavorx® to which a pH modifying agent has been added.

One aspect of this invention is to further aid absorption by using saliva and/or other mucosal fluids to be the immediate carrier of the pH modifier and, using a rapidly dissolving coating on the exterior or near the exterior of the dosage units, precondition the surrounding saliva and fluids to near a pH level determined with reference to the pKa of the given drug, thereby establishing an initial pH prior to the availability of conventional buffer systems. In this way, absorption is facilitated almost immediately. This methodology would apply to all solid dosage units including without limitation capsules, liquigels, tablets, thin film, sheet, orally dissolving tablets, vaginal rings, suppositories, pessaries, topicals, microparticles, particles and the like. This would also apply to nasal, ophthalmic, aural, rectal and vaginal dosage units.

Similarly, the same method may be used according to another aspect of the present invention to adjust pH so as to retard absorption, including in a specific area. As noted above, it may be desirable to retard absorption of an antagonist which could be absorbed sublingually in the mouth (e.g. naloxone).

To date, the coating art has been used in the pharmaceutical field principally as a way of delaying the disintegration of a dosage form and or for the protection of the bioactive agent in vivo until absorbed. For example an enteric coating is a barrier applied to oral medication that controls the location in the digestive system where it is absorbed. Enteric refers to the small intestine; therefore enteric coatings prevent release of medication before it reaches the small intestine. Most enteric coatings work by presenting a surface that is stable at the highly acidic pH found in the stomach, but breaks down rapidly at a less acidic (relatively more basic) pH. Materials used for enteric coatings include fatty acids, waxes, shellac and plastics, plant fibers, etc. (see, e.g. Sands et al US 2004/0162263 A1; Herbig et al 6,609,590; Lew 5,364,634; Oshlack et al 6,387,404; Ullah et al 6,331,316 (each of which is incorporated herein by reference). When enteric coatings are used the pH modification layer is immediately under the enteric coating. If further assurance of non-buccal absorption is required then the pH modifying layer can be exterior to the enteric coating. The pH modifier of this invention is not part of the granulation in a solid dosage form as this granulation would include the usual internal dynamic buffer system that is known in the art.

Coatings may be applied Neither to the dosage form or to the drug particles themselves. In taste masking, a light coating may be applied such that the taste of the drug is masked when in the mouth (in the case of a quick dissolve dosage form), but is quickly released in the gastrointestinal tract.

One aspect of the present invention is to allow for the application of a rapid release and rapid acting pH modulating coating for the saliva or mucosal fluid, on a solid dosage form. In one embodiment, a pH agent (either an acid or base or neutral agent) together with a rapidly dissolving polymer is coated on the exterior of the dosage form. The polymer dissolves promptly when wetted by saliva and rapidly releases the pH agent and thereby rapidly modulates the pH of the saliva. By immediately optimizing pH for drug absorption, delivery of the bioactive agent is enhanced or, in the case of multiple bioactives in one dosage unit, it may enhance one and retard one or more others. The use of multiple bioactives is seen in many opiate drugs that are taken orally and include an antagonist. The goal here is to use the pH to absorb the active and little if any of the antagonist when the oral dose is taken orally. If the oral dose is abused intravenously, the antagonist blocks the opiates actions.

This invention applies to all dosage forms. It has particular application to oral mucosally absorbed forms as well as others. It can also serve to aid oral quick dissolve forms, such as quick dissolve films, which are to be swallowed but in which it is not desirable to absorb the bioactive in the mouth. In this case the pH coating can condition to hinder the absorption. In this embodiment, the rapid release coating contains a material having a property of rapidly modulating a pH of bodily fluids in which the material comes in contact in a direction toward the least effective absorptive pH in keeping with the Henderson Hasselbach equation relating to a particular drug.

It is expressly contemplated that one or more pH agents may be incorporated into the rapid release coating. It is also contemplated that an acid/base combination—referred to in the art as a "dynamic buffering system" may be included in the rapid release coating (see Fuisz U.S. Patent Application Publication No. 2009/0098192 A1 discussing dynamic buffering and incorporated herein by reference). The pH agent may include any material—or combination of materials—useful to modify pH; however since the role of this coating is as a "strike force" it may not need the reserve amounts of the dynamic equation in a true dynamic buffering system.

It is further contemplated that the rapid release coating of the present invention may be applied as a pre-coating prior to a coating that is aimed, like an enteric coating, at delaying disintegration of the dosage form. An enteric coating is a barrier applied to oral medication that controls the location in the digestive system where it is dissolved; enteric coatings prevent release of medication before it reaches the small intestine.

In such an embodiment, after the enteric coating (or similar coating) dissolves, the rapid release coating would then rapidly release the pH modulating agent. Of course, in this embodiment, the pH modulating agent would be acting upon gastric juices as distinct from saliva as is the case in the primary embodiment. Other mammalian uses, such as and without limitation vaginal or nasal or respiratory or ophthalmic or aural use would involve the local fluids.

It is further contemplated that the enteric coating and pH modulating agent can be combined.

By "rapid release" is meant that the coating will dissolve rapidly in the intended medium—within approximately ninety seconds, preferably within approximately thirty seconds, more preferably within approximately 20 seconds and most preferably within 10 seconds. The effect on pH will be nearly instantaneous with the release of the pH agent.

As used herein the method of "coating" may include spray coating, spray drying, dip coating or any other currently known or future developed coating method. For film use the "coating" may well be applied during the drying process. For sheet use it may be applied as it leaves an extruder or similar device.

The coating may be a polymer or a saccharide but is not limited to them because anyone skilled in the art can use whatever coating material that functions well. Various combinations of materials may be used for the coating material.

It is important to state here that an internal buffer system which is in common use, is part of the recipe of the granulation and is therefore released "in part" as the dosage form dissolves whereas the "coating" which is referenced here is on the front line—dissolving rapidly and in its entirety and therefore having a quick and optimal pH effect on the surrounding fluids. Thus, the coating can contain a material having a property of rapidly modulating a pH of bodily fluids in which the material comes in contact in a direction towards an ideal absorptive pH (or in another aspect of the invention towards an ideal pH for hindering absorption) of the at least one bioactive agent that one desires to be absorbed. By "rapidly modulating a pH," we mean changing the pH by at least 1.5, preferably at least 2, more preferably at least 3, most preferably at least 4, in 20 seconds. By "in a direction towards an ideal absorptive pH of the at least one bioactive agent that one desires to be absorbed," we mean that the pH moves (i.e., lower or higher) at the start of release from the starting pH of the bodily fluid (without the core dose in contact therewith) in a direction of an ideal absorptive pH (or in another aspect of the invention tan ideal pH for hindering absorption) given the pKa of the at least one bioactive agent and considering whether the at least one bioactive agent is acidic or basic (e.g., weak acid or weak base), and may, with continued release, approach, reach and exceed the ideal absorptive pH of the at least one bioactive agent, the absorption of which one wants to maximize (or hinder). Thus, the goal would be to modulate the pH near the ideal absorptive pH for a given drug and then let the internal dynamic buffer system take over and fine-tune the pH; however, as with any medication, patient size, individual physiology, other medications, foods, drink, etc. may cause an overshoot or undershoot.

While the present application refers to "pKa," since the sum of pKa and pKb equals 14 at 25° C. in an aqueous solution, reference to pKa should be taken as a short-hand reference to either pKa or pKb, since if one is known, the other can be easily calculated.

The ideal absorptive pH is the pH at which 50-70%, preferably at least 80%, more preferably at least 90%, most preferably at least 99% of the bioactive is nonionized. The ideal pH for hindering absorption is the pH at which 50-70%, preferably at least 80%, more preferably at least 90%, most preferably at least 99% of the bioactive is ionized.

While the primary embodiment is directed at rapidly controlling the pH of the saliva, the invention may equally apply to vaginal fluids, gastric juices, ophthalmic fluids, nasal fluids, respiratory fluids and other bodily fluids of a mammal.

It is expressly contemplated that the present invention may be applied to drug particles or microparticles, wherein each particle or microparticle is functioning and structured as an individual dosage unit. In this case the microparticle may be coated with a pH modulator even though the particle itself may contain an accessory dynamic buffer system. This is directly applicable to certain new approaches that deposit bioactive particulates and vapors on the nasal mucosa. It also has an important application to topical absorption wherein the pH modulation enhances the activity or hinders the activity of one or more bioactives.

This application applies to all bioactive forms including nicotine, tobacco, materials derived from tobacco and any type container or vehicle containing same, including a pouch type delivery vehicle. The pouch of the tobacco pouch delivery system is an ideal vehicle to modify buccal pH towards that which favors nicotine absorption. In a pouch tobacco product the pH modifier as described above may be on the pouch, or in the pouch material or on the tobacco or nicotine therein.

If the dosage unit contains more than one bioactive agent, e.g., an opiate and an antagonist, the material having the property of rapidly modulating a pH of bodily fluids in which the material comes in contact rapidly can modulate a pH of bodily fluids towards an ideal absorptive pH of one bioactive agent given the pKa (e.g., the opiate) and rapidly modulate a pH of bodily fluids away from an active pH range, given the pKa, of another bioactive agent (e.g., the antagonist).

In another embodiment, the pH system may be delivered in a modified liquid that is taken prior to, at the same time, or following the administration of a solid dosage form (see Fuisz U.S. Pat. No. 6,337,083 (Oral delivery method and composition for solid medications or dietary supplement)) in which one of the current inventors teaches a swallowing aid, the full text of which is incorporated herein by reference as if fully stated).

This liquid pH system may be combined with the invention of U.S. Pat. No. 6,337,083 in a single liquid.

The liquid system embodiment is, in a sense, the ultimate embodiment of the rapid release coating—with the liquid, the pH system has already been released into the liquid medium.

Special mention must be made that in U.S. Pat. No. 6,337,083, the liquid is modified to aid in the swallowing of a solid oral dosage unit and by adding pH modification of this invention, it becomes a new entity in terms of advancing absorption or in the case of say the bisphosphonates which are excoriating to the esophagus and which are active at a very acidic pH so that modifying the saliva to a neutral or basic pH serves to retard any absorption in the esophagus. This pH modifier can also be added to a product like Flavorx®, which is used in compounding a liquid dosage unit in order to improve the taste profile and therefore also serve to modify or retard absorption.

In addition to modifying the pH of liquids such as that described in U.S. Pat. No. 6,337,083 and Flavorx®, the present invention contemplates modifying the pH of any liquid, whether used for ease of swallowing of solid dosage forms or for flavoring or other purposes, such that the modified liquid directly, indirectly or by dilution provides a pH which promotes (or hinders in another embodiment) the bioactive dose.

As with the rapid release coatings for solid dosage forms disclosed herein, the liquid pH system may be used to enhance absorption or hinder absorption as set forth herein. For example, one application is to use with a product like Fosamax® to retard absorption of the drug in the esophagus by modifying the pH of the esophageal mucosa so as to discourage or hinder drug absorption. The liquid may further act through an alternate modality by modifying pH to prevent or hinder disintegration of the tablet (or other solid dosage form) itself, where the dosage form disintegrates less quickly at certain pHs.

Additionally, the liquid system may be used to treat the pH of the oral cavity and GI tract prior to, during or after the administration of a bioactive, e.g., a solid bioactive dose to promote or hinder absorption of the bioactive.

Because of the sheer mass of the liquid system, the liquid may be preferable to the rapid release coating where large changes in the GI tract pH are desired.

It is expressly contemplated that the liquid may be pre-manufactured and bottled, or made on demand using a package of ingredients. For example, the pH of the liquid may be controlled at the same time a flavor package is inserted, such as those made by Flavorx®.

Thus, the modified liquid is one the pH of which has been modified, e.g., during its production at or prior to bottling or at the time of administration by including a pH modifier particularly selected to control the effective pH of the liquid in a predetermined range to help or hinder absorption.

The most common method of administration of the liquid or solid composition of the present invention will be to the oral mucosa. However, the pharmaceutical composition may be administered in the vagina, rectum, ophthalmic, aural, nose, topically, respiratory tree, within the GI tract or any other drug delivery location. The pH modifier may also be used in a douche type product which will affect the absorption of a gel or solid dosage form then used vaginally.

The pH modifier may be any material that has the required pH and can be safely administered to a mammal. Examples of such materials include but are not limited to malic acid, caustic soda, etc. Other materials useful as a pH modifier would be known to those skilled in the art based on the teachings in the present specification.

The pH modifier may be present in an amount that brings about the rapid modulation of the pH of bodily fluids in which the material comes in contact in a direction towards (or away from) an ideal absorptive pH of the at least one bioactive agent that one desires to be absorbed given the pKa of the bioactive agent. That amount will vary depending on the type of administration, the bioactive agent, the dosage form, etc. but can be determined by those skilled in the art by routine experimentation based on the teachings provided in this specification.

While the invention is primarily directed at drug application, it is expressly contemplated that the invention may be used within any bioactive agent. The bioactive agent of the present invention may be any pharmaceutical, biological, antigenic, antibody, botanical, tobacco, food or nutraceutical, cosmaceutical or other active agent.

Examples of pharmaceutical bioactive agents include, but are not limited to ace inhibitors, such as Benazepril, Captopril, Enalapril, Lisinopril, Moexipril, Perindopril, Quinapril, Ramipril and Trandolapril; acne treatments, such as adapalene, azelaic acid, BenzaClin, Benzamycin, Benzoyl Peroxide, clindamycin, Duac, Erythromycin, Glycolic Acid, Isotretinoin, Sulfacetamide with sulfur, Tazarotene and Tretinoin; actinic keratosis, such as declofenac, fluorouracil; addiction aids, such as buprenorphine, Disulfiram, Naltrexone, Suboxone and varenicline; aldosterone antagonists, such as eplerenone and spironolactone; alpha-1 adrenergic blockers, such as alfuzosin, doxazosin, prazosin, tamsulosin and terazosin; ALS agents, such as riluzole; Alzheimer's Disease medications, such as donepezil, Galantamine, rivastigmine, tacrine and memantine; anesthetics, such as dexmedetomidine, etomidate, ketamine, methohexital, pentobarbital, propofol and thiopental; angiotensin II receptor blockers, such as candesartan, eprosartan mesylate, irbesartan, losartan, olmesartan, telmisartan and valsartan; antacids, such as Aluminum hydroxide, AlOH and magnesium trisilicate; anti-arrhythmics, such as adenosine, amiodarone, Atropine, Bretylium, digoxin-Immune Fab, disopyramide, dofetilide, epinephrine, Esmolol, flecainide, ibutilide, isoproterenol, lidocaine, mexiletine, moricizine, procainamide, propafenone, quinidine, sotalol, tocainide and verapamil; antibiotics, such as Aztreonam, TMP/SMX, Chloramphenicol, Clindamycin, Dapsone, Daptomycin, Ertapenem, Imipenem/cilastatin, Linezolid, Meropenem, Metronidazole, Nitrofurantoin, Quinupristin/Dalfopristin, Rifaximin, Tigecycline, Telithromycin and Tinidazole; anticholinergic acids, such as Dicyclomine, Donnatal, Flavoxate, Glycopyrrolate, Hyoscyamine, Oxybutynin, Propantheline and Tolterodine; anticonvulsants, such as carbamazepine, clonazepam, diazepam, ethosuximide, felbamate, fosphenytoin, gabapentin, levetiracetam, lamotrigine, lorazepam, Oxcarbazepine, Phenobarbital, phenytoin, pregabalin, primidone, tiagabine, topiramate and valproic acid; antidepressants, such as amitriptyline, buproprion, citalopram, desipramine, doxepin, duloxetine, escitalopram, fluoxetine, fluvoxamine, imipramine, mirtazapine, nefazodone, nortriptyline, nortriptyline, sertraline, trazodone and venlafaxine; anti-diarrheals, such as dephenoxylate+atropine, Imodium and bismuth subsalicylate; anti-emetics, such as Aprepitant, dolasetron, droperidol, granisetron, metoclopramide, ondansetron, prochlorperazine, scopolamine and trimethobenzamide; antifungals, such as Ampho B, Ampho B lipid, anidulafungin, caspofungin, Clotrimazole fluconazole, flucytosine, Griseofulvin, Itraconazole, ketoconazole, Micafungin, nystatin, Posaconazole, terbinafine, voriconazole, butenafine, ciclopirox, clotrimazole, enconazole, ketoconazole, Miconazole, naftifine, nystatin, oxiconazole terbinafine and Tolnaftate; anti-hepatitis, such as adefovir, entecavir, lamivudine, peginterferon alfa-2a, peginterferon alfa-2b, Rebetron and ribavirin; antiherpetic agents, such as Acyclovir, famciclovir, valacyclovir, acyclovir, docosanol and penciclovir; antihistamines, such as cetirizine, desloratadine, fexofenadine, loratadine, chlorpheniramine, clemastine, cyproheptadine, dimenhydrinate, diphenhydramine, hydroxzine and promethazine; anti-hypertension, such as Benazepril & HCTZ, Captopril & HCTZ, Enalapril & HCTZ, Lisinopril & HCTZ, Moexipril & HCTZ, Losartan & HCTZ, Valsartan & HCTZ, Atenolol & chlorthalidone, Bisoprolol & HCTZ, Metoprolol & HCTZ, Nadolol & bendroflumethazide, Propranolol & HCTZ, Timolol & HCTZ, Amlodipine & benazepril, Verapamil & trandolapril, Amiloride & HCTZ, Spironolactone & HCTZ, Triamterene & HCTZ, Clonidine & chlorthalidone, Hydralazine & HCTZ, Methyldopa & HCTZ and Prazosin & polythiazide; antihypertensives, such as Aliskiren, Aliskiren, epoprostenol, fenoldopam, hydralazine, minoxidil, nitroprusside, phentolamine and treprostinil; anti-influenza agents, such as amantadine, oseltamivir phosphate, rimantadine and zanamivir; antimalarials/anti-protozoals/amebicides, such as Atovaquone, Chloroquine, Iodoquinol, Mefloquine, Primaquine, Pyrimethamine, Pyrimethamine -Sulfadoxine and Quinine Sulfate; anti-platelet agents, such as abciximab, dipyridamole/ASA, anagrelide, cilostazol, clopidogrel, dipyridamole, eptafibatide, ticlopidine and tirofiban; antipsychotics, such as aripiprazole, chlorpromazine, Clozapine, fluphenazine, haloperidol, loxapine, molindone, olanzepine, perphenazine, pimozide, quetiapine, risperidone, thioridazine, thiothixine, trifluoperazine, ziprasidone and Lithium; antispasmotics, such as Dicyclomine, Donnatal Extentabs, Propantheline, Simethicone, hyoscyamine, Librax, tegaserod and Bellergal-S; anti-tussives/expectorants, such as Benzonatate and guaifenesin; atopic dermatitis medications, such as pimecrolimus and tacrolimus; benzodiazepines and non-benzodiazepine sedatives, such as alprazolam, buspirone, chlordiazepoxide, chlorazepate, clonazepam, diazepam, estazolam, eszcpiclone, flurazepam, lorazepam, midazolam, Oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol and timolol; bile acid sequestrants, such as cholestyramine, colesevelam and colestipol; bisphosphonates, such as alendronate, etidronate, pamidronate, risedronate, tiludronate and Zoledronic acid, Raloxifene and Teriparatide; bladder spasm medications, such as flavoxate, hyoscyamine, darifenacin, oxybutynin, solifenacin, tolterodine and trospium; benign prostatic hypertrophy medications, such as alfuzosin, doxazosin, dutasteride, finasteride, tamsulosin and terazosin; burn preparations, such as mafenide acetate and silver sulfadiazine; calcium channel blockers, such as amlodipine, bepridil, diltiazem, felodipine, isradipine, nicardipine, nifedipine and nisoldipine; calcium supplements, such as Calcium and Hypocalcemia; cephalosporins, such as Cefadroxil, Cefazolin, Cephradine, Cephalexin, Cefaclor, Cefotetan, Cefoxitin, Cefprozil, Cefuroxime, Cefuroxime, loracarbef, Cefdinir, Cefixime, Cefoperazone, Cefotaxime, Cefpodoxime, Ceftazidime, Ceftibuten, Ceftizoxime and Cefepime; colony stimulating factors, such as darbepoietin alfa, erythropoietin, filgrastim, oprelvekin, pegfilgrastim and sargramostim; corticosteroids, such as Budesonide, cortisone acetate, dexamethasone, fludrocortisones, hydrocortisone, methylprednisolone and prednisone; corticosteroids Intra-articular, such as Depo-Medrol and Triamcinolone Acetonide; cystitis, such as pentosan polysulfate, Bethanecol and Alum irrigation; decongestants, such as Phenylephrine and Pseudoephedrine; anti-diabetic agents, such as acarbose, Miglitol and metformin, Avandamet.RTM., Glucovance, Metaglip, Metaglip, rosiglitazone, osiglitazone, repaglinide, Chlorpropamide, glimepiride, glyburide, glipizide, Tolazamide, Tolbutamide, Glucagon, extenatide and pramlintide; direct thrombin inhibitors, such as argatroban, Bivalirudin and lepirudin; disease modifying agents, such as adalimumab, anakinra, auranofin, azathioprine, etanercept, hydroxychloroquine, infliximab, leflunomide, methotrexate and sulfasalazine; diuretics, such as Acetazolamide, Amiloride, Amiloride and HCTZ Bendroflumethiazide, Bumetanide, Chlorothiazide, Chlorthalidone, Dichlorphenamide, Eplenerone, Ethacrynic acid, Furosemide, Hydrochlorothiazide, HCTZ/Triampterene, Hydroflumethiazide, Indapamide, Methazolamide, Methyclothiazide, Methyclothiazide, Metolazone, Polythiazide, Spironolactone, Spironolactone, HCTZ Torsemide, Trichlormethiazide and Triamterene; endocrine agents, such as bromoc cinacalcet cosyntropin, riptine, cabergoline, calcitonin, desmopressin, Leuprolide, octreotide and vasopressin; erectile dysfunction agents, such as Sildenafil, tadalafil, vardenafil; fever medications, such as allopurinol, antihistamines, azathioprine, barbiturates, carbamazepine, cephalosporins, cimetidine, folic acid, hydralazine, hydroxyurea, ibuprofen, isoniazid, methyldopa, nitrofurantoin, penicillins, phenytoin, phenytoin, procainamide, prophylthiouracil, quinidine, streptomycin sulfonamides, sulindac, triamterene and vancomycin; fibrates, such as clofibrate, fenofibrat and gemfibrozil; fluoroquinolones, such as Ciprofloxacin, Gatifloxacin, Levofloxacin, Moxifloxacin, Norfloxacin and Ofloxacin; gastrointestinal agents, such as Alosetron, infliximab, Mesalamine, misoprostol, Neomycin, octreotidev, osalazine, Orlistat, sucralafate, Sulfasalazine and vasopressin; gout treatments, such as allopurinol, colchicine, probenecid, Rasburicase and sulfinpyrazone; H2 receptor blockers, such as cimetidine, famotidine, nizatidine and ranitidine; aAnti-herpetic agents, such as Acyclovir, famciclovir, valacyclovir, acyclovir, docosanol and penciclovir; hypertensive urgency, such as Captopril, Clonidine and Labetalol; hypertensive emergency, such as Enalaprilat, Esmolol, Fenoldopam mesylate, Hydralazine, Labetalol, Nicardipine, Nitroglycerin and Sodium nitroprusside; hemorrhoidal preparations, such as Anusol HC, Anusol Suppository, Dibucaine, pramoxine 1%, Proctofoam-HC and Analpram-HC; inflammatory bowel disease agents, such as balsalazide, budesonide, infliximab, mesalamine, olsalazine and sulfasalazine; Interferon, such as Interferon Alfa-2A, Interferon Alfa-2b, Interferon Alfa-2b and Ribavirin combo Pack, Interferon Alfa-N3, Interferon Beta-1A, Interferon Beta-1B (Betaseron); intermittent claudication, such as cilostazol and pentoxifylline; immunizations, such as Comvax, diphtheria-tetanus toxoid, Hepatitis A vaccine, Hepatitis B vaccine, Influenza vaccine, Fluzone, Lyme disease vaccine, PNEUMOVAX* 23; laxatives, such as Bisacodyl, Cascara, Docusate, Fleet Phospho-Soda, Glycerin, Lacalutose, lubiprostone, Magnesium citrate, Magnesium hydroxide—MOM, Mineral Oil, Pericolace, Psyllium and Senna; low molecular weight heparins, such as dalteparin, danaparoid, enoxaparin, tinzaparin, fondaparinux; macrolides, such as Azithromycin, Clarithromycin and Erythromycin; magnesium, such as magnesium salt; migraine treatments, such as almotriptan, eletriptan, frovatriptan, naratriptan, rizatriptan, sumatriptan, zolmitriptan, Cafergot.RTM., Cafergot.RTM., dihydroergotamine and Midrin.RTM.; mouth and lip treatments, such as amlexanox, Benzocaine, carbamide, peroxide, Kenalog in Orabase.RTM., Phenol, chlorhexidine gluconate, clotrimazole, Nystatin, Penciclovir, docosanol, Gelclair, lidocaine viscous, BMX Cocktail, Pilocarpine and Artificial saliva; multiple sclerosis treatments, such as glatiramer, interferon beta-1A and interferon beta-1B; muscle relaxants, such as baclofen, carisprodol, cyclobenzaprine, cyclobenzaprine, Diazepam, Metaxalone, Methocarbamol, Orphenadrine; nasal preparations, such as azelastine, beclomethasone, budesonide, cromolyn, desmopressin acetate, flunisolide, fluticasone, Ipratropium bromide, mometasone, oxymetazoline, phenylephrine, Saline nasal spray, Sumatriptan, triamcinolone and Zolmitriptan; urology treatments, such as Belladonna and opium, flavoxate, hyoscyamine, hyoscyamine, oxybutynin, solifenacin, tolterodine and trospium; neuromuscular blockers, such as Atracurium, Cisatracurium, doxacurium, mivacurium, pancuronium, Rocuronium, Succinylcholine, vecuronium, Mivacurium, Rapacuronium, Rocuronium, Succinylcholine, Atracurium, Cisatracurium, Pancuronium, Vecuronium, Doxacurium, Pipecuronium and Tubocurarine; nitrates, such as Isosorbide dinitrate, Isosorbide mononitrate, Nitroglycerin ointment, Nitrobid and Nitroglycerin transdermal; NSAID's, such as Arthrotec, diclofenac, Etodolac, indomethacin, Ketorolac, Sulindac, Tolmentin Diflunisal Salsalate Meloxicam, piroxicam, Nabumetone Flurbiprofen, Ibupropen, Ketoprofen, Naproxen, Oxaprozin, celecoxib, Rofecoxib and Valdecoxib; ophthalmic agents, such as, proparacaine, tetracaine, Ciprofloxacin, Erythromycin, Gentamcyin, levofloxacin, levofloxacin, norfloxacin, Ofloxacin, Polysporin.RTM., Polytrim, Sulfacetamide, Tobramycin, Blephamide.RTM., Blephamide.RTM., Maxitrol.RTM., Pred G.RTM. and Tobra-Dex.RTM., Dexamethasone, Fluorometholone, Loteprednol, Prednisone, Rimexolone, azelastine, Cromolyn sodium, emedastine, Epinastine, Ketotifen Fumarate Ophthalmic Solution 0.025%, Levocabastine, Lodoxamide tromethamine, Naphazoline, Naphcon-A.RTM., nedocromil, Olopatadine, pemirolast, Betaxolol, Betaxolol, Levobunolol, Timolol, Brinzolamide, Dorzolamide, Pilocarpine, bimatoprost, Latanoprost, travoprost, unoprostone, Apraclonidine, Brimonidine, Cosopt.RTM. and Cosopt.RTM., Atropine, Cyclopentolate, Homatropine, Phenylephrine, Phenylephrine, Diclofenac, Flurbiprofen and Ketorolac; ear (otic) preparations, such as Auralgan.RTM., carbamide peroxide, CIPRODEX.RTM., Ciprofloxacin and hydrocortisone, Cortisporin.RTM., Ofloxacin, Triethanolamine and Vosol Otic.RTM.; opiates, such as Codeine Fentanyl Hydrocodone Hydrocodone, Meperidine Methadone, morhphine, xycodone, Propoxyphene, Darvon.RTM., Fioricet, Fiorinal, Soma compound, Tramadol, Anexsia, Darvocet, Darvon Compound, Lorcet, Lortab, Percocet, Percodan, Roxicet, Tylenol with Codeine, Tylox, Vicodin, Wygesic, Buprenorphene, Butorphanol, Dezocine, Nalbuphine, Pentazocine, Nalmefene Naloxone, Suboxone.RTM. and Ziconotide; parkinson's disease treatments, such as amantadine, benztropine, bromocriptine, entacapone, pergolide, pramipexole, ropinirole, selegiline, Sinemet.RTM., tolcapone and trihexyphenidyl; PCA—Patient Controlled Analgesia, such as Fentanyl, Hydromorphone, Meperidine and Morphine; penicillin's, such as Ampicillin, Ampicillin/sulbactam, Amoxicillin, Amoxicillin/Clavulanate, Cloxacillin, Dicloxacillin, Nafcillin, Penicillin G, Penicillin VK, Piperacillin, Piperacillin/Tazobactamm, Ticarcillin, and Ticarcillin/Clavulanate; phosphate supplementation, such as, K-Phos.RTM. Neutral Tablets, K-PHOS.RTM. ORIGINAL, Neutra-Phos.RTM.; potassium supplementation, such as K-LOR, Klor-Con.RTM., Potassium depletion; prostate cancer medications, such as bicalutamide, flutamide, goserelin, leuprolide and nilutamide; proton pump inhibitor's, such as esomeprazole, Lansoprazole, Omeprazole, Pantoprazole and Rabeprazole Sodium; psoriasis medications, such as acitretin, alefacept, Anthralin, Calcipotriene, efalizumab and Tazarotene; renal failure medications, such as Aluminum Hydroxide, Calcium acetate, Calcitriol, Doxercalciferol, Ferric Sodium Gluconate, paricalcitol and sevelamer; pulmonary medications, such as ipratropium, tiotropium, albuterol, bitolterol, levalbuterol, pirbuterol, metaproterenol, formoterol, salmeterol, Advair.RTM., Symbicort.RTM., beclomethasone, budesonide, flunisolide, fluticasone, Mometasone furoate, triamcinolone, montelukast Singulair.RTM., zafirlukast, cromolyn sodium, nedocromil, acetylcysteine and aminophylline/theophylline; disease modifying agents, such as adalimumab, anakinra, auranofin, azathioprine, etanercept, hydroxychloroquine, infliximab, leflunomide, methotrexate and sulfasalazine; HMG COA reductase inhibitors, such as Atorvastatin, Fluvastatin, Lovastatin, Pravastatin, Rosuvastatin, Simvastatin, Advicor.RTM., Vytorin.RTM. and ezetimibe; stimulants, such as atomoxetine, benzphetamine, Caffeine, dexmethylphenidate, Dextroamphetamine, diethylpropion, Methylphenidate, Modafinil, Pemoline, phendimetrizine, phentermine and sibutramine; tetracyclines such as Doxycycline, Minocycline andTetracycline; thrombolytic agents such as Alteplase; anti-thyroid agents such as methimazole and propylthiouracil; toxicology related medications such as acetylcysteine, Charcoal, deferoxamine, digoxin immune fab, flumazenil, fomepizole, methylene blue, naloxone, sodium polystyrene sulfonate and Sorbitol; anti-mycobacterial agents such as Ethambutol, Isoniazid, Pyrazinamide, rifabutin, Rifamate, Rifampin, Rifapentine and Rifater; topical products such as Alitretinoin, Becaplermin, Calamine, Capsaicin, Doxepin, lidocaine/prilocaine, fluorouracil, Masoprocol, Pimecrolimus, Selenium sulfide and Tacrolimus; topical anti-viral agents such as acyclovir, docosanol, imiquimod, penciclovir, podofilox and podophyllin; topical antibacterials such as bacitracin, metronidazole, mupirocin, bacitracin/neomycin/polymyxin, bacitracin/polymyxin and silver sulfadiazine; topical antifungals such as butenafine, ciclopirox, clotrimazole, econazole, ketoconazole, miconazole, naftifine, nystatin, oxiconazole, terbinafine and tolnaftate; topical antiparasitic agents such as Crotamiton, Lindane, Permethrin, pyrethrins and piperonyl butoxide; topical burn preparations such as mafenide acetate and silver sulfadiazine; topical corticosteroids such as Aclometasone diproprionate, Desonide, Flucinolone acetonide, Hydrocortisone, Betamethasone dipropionate, betamethasone valerate, clocortolone pivalate, desoximetasone, fluocinolone acetonide, flurandrenolide, fluticasone propionate, Chydrocortisone butyrate, hydrocortisone valerate, mometasone furoate, prednicarbate, triamcinolone, amcinonide, augmented betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate; urology medications such as pentosan polysulfate, Bethanecol and phenazopyridine; vaginal preparations such as clindamycin, metronidazole, butoconazole, clotrimazole, miconazole, terconazole and tioconazole; vasodilators such as Fenoldopam mesylate, Hydralazine, Nesiritide, Nicardipine, Nitroglycerin, and Sodium Nitroprusside; and vasopressors and inotropes such as Dobutamine, Dopamine, Epinephrine, inamrinone, Milrinone, Norepinephrine, Phenylephrine, and Vasopressin.

Examples of food or nutraceutical bioactive agents include, but are not limited to, constituents in foods or dietary supplements that are responsible for changes in health status, such as components of plants, especially fruits and vegetables, e.g., soy which contains isoflavones and phytoestrogens, tomatoes which contain lycopene that may have anticancer properties, berries such as blueberries and raspberries which contain flavonoids like anthocyanins that may act as antioxidants, green tea which contains epigallocatechin gallate (EGCG) that may have anticancer properties, resveratrol from red grape products as an antioxidant, soluble dietary fiber products, such as psyllium seed husk for reducing hypercholesterolemia, broccoli (sulforaphane) as a cancer preventative, and soy or clover (isoflavonoids) to improve arterial health. Flavonoids, antioxidants, alpha-linolenic acid from flax seeds, extracts such as ginseng, garlic oil, etc. Ph modifier coating may be applied in foods for better nutrient absorption as well as for improvement of flavor.

Examples of biological bioactive agents include, but are not limited to biologically active substances in plants that have proven (e.g. cholesterol lowering effects of phytosterols) or potential beneficial effects on health, i.e., phytochemicals or phytonutrients, in particular phytochemicals in leaves, stems, roots, tubers, buds, fruits, seeds and flowers, and plant derived foods and drinks (such as tea, coffee, alcoholic beverages), such as flavonoids found in a range of plant derived foods including tea, wine, onions, apples and berries, glucosinolates from Cruciferous vegetables, phenolic acids in tea and coffee for example, and carotenoids (some of which are precursors of vitamin A) prevalent in red, green and orange fruits and vegetables.

Examples of antigen bioactive agents include, but are not limited to exogenous antigens, endogenous antigens, autoantigens and tumor antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4.sup.+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic CD8.sup.+T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. An autoantigen is usually a normal protein or complex of proteins (and sometimes DNA or RNA) that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients. Tumor antigens or Neoantigens are those antigens that are presented by MHC I or MHC II molecules on the surface of tumor cells. These antigens can sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens can also be on the surface of the tumor in the form of, for example, a mutated receptor, in which case they will be recognized by B cells.

Examples of botanical bioactive agents include, but are not limited to PMI-004 (advanced botanical formulation for type II diabetes that represents a multi-mechanism bioactive that: 1) in adipocytes increases adiponectin secretion, 2) in the liver lowers PEPCK expression, and 3) in muscle cells increases cellular signaling through the insulin receptor pathway, increasing glucose uptake, glycogen synthase, and glycogen accumulation), PMI-005 (botanical bioactive, derived from a common vegetable, that inhibits gene expression of a variety of pro-inflammatory cytokines (including a-TNF, i-NOS, IL-1b, and COX-2) that are currently undergoing a human clinical trial in osteoarthritis may also may have utility in the management of severe/life threatening inflammatory conditions, such as in the management of the septic patient), PMI-006 (botanical bioactive, derived from a spice, that inhibits a range of inflammation-related enzymes (including a-TNF and COX-2) and also possesses range of novel bioactivities related to both lipid and glucose metabolism (RXR receptors)), PMI-007 (a powerful, centrally acting, botanical appetite suppressor which acts via a unique central pathway in the nutrient-sensing hypothalamic neurons by increasing ATP content/production, possesses potent anorectic activity without typical CNS appetite suppressor side effects and pre-clinical data for which has shown that the agent suppresses both appetite and reduces weight in animal models, while there is supporting clinical evidence of human efficacy), PMI-008 (botanical bioactive, derived from an agricultural waste processing stream, that blocks fat accumulation/absorption and promotes weight loss via interaction with a variety of lipases including PL, LPL, and HSL), and PMI-016 (a powerful, plant-derived anabolic/ergogenic agent, with no androgenic side effects; could be used in a range of human muscle wasting disorders, including those associated with both cancer and AIDS, as well as general aging (sarcopenia);

has been shown to induce protein synthesis in muscle cells (similar to IGF) and promote a reduction in protein degradation, while it has also been shown to increase growth hormone gene transcription and decrease in ubiquitin protein ligase gene transcription; and shows no binding to testosterone receptor in contrast to anabolic steroids). Examples of botanical bioactive agents also include tobacco and all tobacco extracts, as well as nicotine itself.

The FDA defines drugs as products that "cure, treat, mitigate or prevent disease or that affect the structure or function of the human body." Cosmetic products are defined by the FDA as "articles intended to be rubbed, poured, sprinkled, or sprayed on, introduced into, or otherwise applied to the human body . . . for cleansing, beautifying, promoting attractiveness, or altering the appearance." Although cosmaceutical products have properties of both groups, the FDA lumps them under the definition of cosmetics, and they are not recognized as a distinct category. Because cosmaceutical products are not included in the FDA's definition of drugs, they are not subject to the same regulations, restrictions, and testing.

The following materials were used in each of the examples below: Hydroxypropylmethylcellulose (HPMC) 4,000 cps, Spectrum Chemical; Malic Acid Powder from Spectrum Chemical; Caustic soda liquid 50% concentration Rayon grade from Tilley Chemical; Calcium carbonate powder, (brand name CalEssence 80) from Specialty Mineral; Calcium silicate (brand name Hubersob 600) from Akrochem; Malic acid from Spectrum Chemicals; Prehydrated Xantham Gum from Tic Gums; Confectioner sugar from Domino; and Corn starch from Market Pantry. We used a pH meter pH 5 Acorn series from Oakton.

EXAMPLE A

Example A comprises an orally dissolvable tablet (i.e. a quick dissolve tablet) that was coated with a rapid release coating to rapidly modulate saliva pH.

We started with Children's Benadryl Allergy FastMelt Cherry flavor that had a starting mass of 605 mg. This was simply a test mule. We then created an acid dipping solution comprised of: water 87%, malic acid 12%, HPMC 1%. Using an Oakton pH meter, this pH of this solution was measured at pH 2.03. We also created an acid powder coating comprising confectioner sugar 50% and malic acid 50%.

Separately, we created a base dipping solution, comprised of water 91%, caustic soda 8%, HPMC 1% (pH 13.1). We also created a base powder coating compromised of calcium carbonate 29%, calcium silicate 29%, caustic soda 42%

To make the foregoing, the following mixing procedures were used.

For liquid dipping solutions: weigh and add ingredients to water and mix vigorously until HPMC is completely dissolved and wait until solution is clear without lumps and bubbles.

For powder coating mixes: weigh and add ingredients together and mix until ingredients are well dispersed.

In the base powder coating, calcium silicate is used as an absorbent for the liquid caustic soda.

We then employed the following coating procedure. First, dip tablet in liquid solution and remove quickly, shake off excess liquid and allow dry at room temperature. Second before tablet is completely dry, roll tablet in powder coating, shake off excess coating and let dry fully. The weight of tablets after coating was 640 to 650 mg.

The following test was then made by a healthy male volunteer: 1) rinse mouth with water. 2) Accumulate saliva in mouth. 3) Insert tablet in mouth and let stand for 10 seconds to mix with saliva. 4) Insert pH meter probe in mouth and take reading.

The results were as follows. Saliva in mouth at starting point: pH 6.4 Saliva with non-coated tablet after ten seconds: pH 6.22. Saliva with acid coated tablet after ten seconds: pH 2.94. Saliva with base coated tablet after ten: pH 9.13

Thus, it was demonstrated that a quick dissolve tablet could be effectively coated with a rapid release coating that will rapidly modulate the pH of saliva. This coating worked by to increase and decrease pH (in separate embodiments).

EXAMPLE B

Example B comprises a conventional tablet that was coating with a rapid release coating to modulate pH.

The tablet used was Tylenol 8 hr muscle aches and pain. Again, this was simply used as a test mule and not for its Henderson Hasselbach absorptive profile.

Using the same procedures as with Exhibit A, we made a base coating solution comprising: water 91%, caustic soda 8%, HPMC (4000 cps) 1%. The resulting base coating solution pH was: 13.1.

The procedures followed were: 1) Add caustic soda and HPMC to water (water pH 7.5). 2) Mix vigorously to dissolve HPMC 3) Wait until caustic coating solution is clear without bubbles and lumps. 4) Dip tablet in solution and remove immediately. 5) Drain extra solution off tablet. 6) Let tablet dry in ambient room conditions.

A healthy male volunteer tested the tablet as follows: 1) Rinse mouth with water. 2) Accumulate saliva in mouth. 3) Insert pH meter probe in mouth and take reading: pH 6.8. 4) Insert tablet in mouth and let stand for 10 seconds to mix with saliva. 5) Insert pH meter probe in mouth and take reading: pH 8.9

EXAMPLE C

Example C comprises a thin film coated with a rapid release coating to rapidly modulate pH.

We purchased Novartis Triaminic thin strips for children, cough & runny nose. Again, this was simply used as a test mule dosage unit. We weighed the unmodified thin film and found a mass of 50 mg. To determine a pH, we dissolved two strips in 5 grams of water and obtained a reading using an Oakton pH meter of 9.05.

We first attempted to use a liquid coating as was used in Example A but we experienced difficulty in that we were tending to dissolve the strip. So we decided instead to use only a simple powder coating, comprising 50% confectioner sugar and 50% malic acid. Using a healthy male volunteer and an Oakton pH meter, we determined an initial pH saliva in mouth: 6.30. The pH of saliva in mouth was found to be 6.46 after dissolving one virgin piece in mouth (i.e., a strip without coating). The pH of saliva in the mouth was measured at: 4.68 ten seconds after dissolving one slightly coated piece (coated film weight: 65 grams). The pH of saliva in the mouth was measured at 4.14 ten seconds after dissolving one heavier coated piece (coated film weight: 90 grams).

EXAMPLE D

For Example D, we purchased Swedish Snus brand General original with no flavor. This was a test mule. We made a coating solution by mixing the following ingredients: water 91%, caustic soda 8%, HPMC 1% (after mixing, we measured the solution's pH to be 13.06). For reference the city water used had a pH of: 7.45.

The Snus pouch weight as purchased was 0.973 gram. We dipped two Snus pouches in the coating solution, after which they each weighed approximately 1.364 g (they were measured without being dried).

We used the following testing method: 1) put 2 virgin pouches in container and add 10 gram of city water; 2) soak for 10 minutes while squeezing pouches without braking them, Temp: 22.4 centigrade; 3) repeat same procedure with 2 coated pouches, Temp: 22.9 centigrade.

The test results were as follows: for the uncoated pouches: pH: 7.94; and for the coated pouches: pH: 11.02.

The above test was done for matters of convenience in a way that was different from the Examples of A, B, and C. However, it was concluded that coating a tobacco pouch would have the same rapid effect on pH that was seen in the other examples.

It is readily seen from the tobacco example that the present invention can be applied to various cannabis products, whether through the use of loose cannabis in a pouch used in the mouth, or the use of cannabis or a cannabis derived extract or by product contained in a conventional solid dosage form.

EXAMPLE E

A liquid solution was made by combining 100 grams water and 1 gram Swallow Easy™ formula, comprised of 4 parts sugar and one part Tic xantham gum. To this solution was added 1 gram of malic acid. The pH of the solution was measured at 2.77. A healthy male volunteer measured his saliva pH for a baseline measurement of 6.81. Then, he allowed the solution to soak in his mouth akin to a mouthwash rinse for 5 seconds. He then measured the pH of his saliva at 4.59.

We claim:

1. A bioactive dose for delivering a bioactive agent to a mammal, comprising a solid bioactive dosage unit containing at least one bioactive agent including tobacco provided in a pouch and a rapid release coating provided on substantially all of the pouch material or in substantially all of the pouch material, the rapid release coating comprising a material having a property of rapidly modulating a pH of bodily fluids with which the material comes in contact in a direction towards an ideal absorptive pH of the at least one bioactive agent given the pKa of that at least one bioactive agent.

2. The bioactive dose according to claim 1, wherein material in the rapid release coating is acidic.

3. The bioactive dose according to claim 1, wherein material in the rapid release coating is basic.

4. The bioactive dose according to claim 1, wherein the rapid release coating dissolves in 30 seconds or less.

5. The bioactive dose according to claim 1, wherein the rapid release coating dissolves in 20 seconds or less.

6. The bioactive dose according to claim 1, wherein the rapid release coating dissolves in 10 seconds or less.

7. The bioactive dose according to claim 1, wherein the rapid release coating is provided on the pouch material.

8. The bioactive dose according to claim 7, wherein material in the rapid release coating is acidic.

9. The bioactive dose according to claim 7, wherein material in the rapid release coating is basic.

10. The bioactive dose according to claim 7, wherein the rapid release coating dissolves in 30 seconds or less.

11. The bioactive dose according to claim 7, wherein the rapid release coating dissolves in 20 seconds or less.

12. The bioactive dose according to claim 7, wherein the rapid release coating is provided in the pouch material.

13. The bioactive dose according to claim 12, wherein material in the rapid release coating is acidic.

14. The bioactive dose according to claim 12, wherein material in the rapid release coating is basic.

15. The bioactive dose according to claim 12, wherein the rapid release coating dissolves in 30 seconds or less.

16. The bioactive dose according to claim 12, wherein the rapid release coating dissolves in 20 seconds or less.

* * * * *